United States Patent
Vogt et al.

(10) Patent No.: US 9,387,275 B2
(45) Date of Patent: *Jul. 12, 2016

(54) ONE-COMPONENT BONE CEMENT PASTES AND METHODS FOR CURING THEM

(75) Inventors: Sebastian Vogt, Erfurt (DE); Hubert Buchner, Reinheim (DE)

(73) Assignee: Heraeus Medical GmbH, Wehrheim (DE)

( * ) Notice: Subject to any disclaimer, the term of this patent is extended or adjusted under 35 U.S.C. 154(b) by 482 days.

This patent is subject to a terminal disclaimer.

(21) Appl. No.: 12/255,224

(22) Filed: Oct. 21, 2008

(65) Prior Publication Data

US 2009/0105144 A1  Apr. 23, 2009

(30) Foreign Application Priority Data

Oct. 22, 2007  (DE) .......................... 10 2007 050 760
Oct. 30, 2007  (DE) .......................... 10 2007 052 116

(51) Int. Cl.
*A61L 24/06* (2006.01)
*A61K 38/18* (2006.01)
*A61L 24/00* (2006.01)

(52) U.S. Cl.
CPC ......... *A61L 24/0094* (2013.01); *A61L 2430/02* (2013.01)

(58) Field of Classification Search
CPC ............................ A61L 24/0094; C08L 33/10
USPC ................... 514/8.2; 252/500, 513, 519.33; 523/117; 525/50
See application file for complete search history.

(56) References Cited

U.S. PATENT DOCUMENTS

| | | | |
|---|---|---|---|
| 4,093,576 A | 6/1978 | deWijn | |
| 4,396,476 A * | 8/1983 | Roemer et al. | 522/109 |
| 4,545,368 A * | 10/1985 | Rand | A61N 1/406 600/12 |
| 4,657,941 A | 4/1987 | Blackwell et al. | |
| 6,309,420 B1 * | 10/2001 | Preissman | A61B 17/7095 424/423 |
| 7,132,462 B2 * | 11/2006 | Lehmann et al. | 523/109 |
| 2004/0132859 A1 * | 7/2004 | Puckett, Jr. et al. | 523/118 |
| 2005/0123743 A1 * | 6/2005 | Martinazzo | 428/328 |
| 2007/0197683 A1 | 8/2007 | Jia | |

FOREIGN PATENT DOCUMENTS

| | | |
|---|---|---|
| DE | 3441564 A1 | 5/1986 |
| EP | 1502569 A1 | 2/2005 |
| JP | 62-258668 A | 11/1987 |
| JP | 2002161013 A | 6/2002 |
| JP | 2005206471 A | 8/2005 |
| JP | 2006299202 A | 11/2006 |
| JP | 2007209763 A | 8/2007 |
| JP | 2008272042 A | 11/2008 |
| LI | 19706064 A1 * | 8/1998 ............. A61K 6/083 |
| WO | 87/00058 A1 | 1/1987 |
| WO | 2004050131 A1 | 6/2004 |
| WO | 2006008499 A1 | 1/2006 |
| WO | 2006062939 A2 | 6/2006 |
| WO | 2007025633 A2 | 3/2007 |
| WO | 2007040250 A1 | 4/2007 |
| WO | 2007048105 A2 | 4/2007 |
| WO | 2007/064304 A1 | 6/2007 |

OTHER PUBLICATIONS

Vallo, J. Biomed. Mat. Res. Part B, 2004.*
Puska, J. Mat. Sci. Mat. Med., 15, 2004.*
1_6_hexanediol dimethacrylate.pdf.*
Takegami, J. Biomed. Mat. Res., 43, 1998.*
Dede, IEEE Trans. Ind. Elec., 38, 1991.*
English Language Abstract for DE 3441564, May 22, 1986.
English Language Abstract for WO 87/00058, Jan. 15, 1987.
Vallo, CI "Influence of cross-linked PMMA beads on the mechanical behavior of self-curing acrylic cements" Instituto De Investigaciones En Ciencia Y Tecnologia De Materiales, J.B. Justo 4302.
English language abstract for JP 2007-209763 found on esp@cenet.com.
English language abstract for JP 2002-161013 found on esp@cenet.com.
English language abstract for JP 2006-299202 found on esp@cenet.com.
English language abstract for JP 2005-206471 found on esp@cenet.com.
Journal of Biomedical Materials Research, 2000, vol. 53, S. 737-747.
English language abstract for JP 2008-272042 found on esp@cenet.com.
English language abstract for JP 62-258668.

* cited by examiner

*Primary Examiner* — Susan Tran
*Assistant Examiner* — William Craigo
(74) *Attorney, Agent, or Firm* — Norris McLaughlin & Marcus PA

(57) ABSTRACT

One-component bone cement pastes, containing:

AI at least one methacrylate monomer suitable for radical polymerization;

AII at least one polymer that is soluble in AI;

AIII at least one particulate polymer that is insoluble in AI and has a particle size of less than 500 μm;

optionally AIV at least one radical-forming initiator or at least one radical initiator that is soluble in AI and subject to thermal decomposition;

optionally AV at least one electrically conductive radio-opaquer, in the form of ferromagnetic particles.

13 Claims, No Drawings

ONE-COMPONENT BONE CEMENT PASTES AND METHODS FOR CURING THEM

The subject matter of the invention are one-component bone cement pastes and methods for curing them.

PMMA bone cements have been known for decades and are based on the groundbreaking work of Sir Charnley (Charnley, J.: Anchorage of the femoral head prosthesis of the shaft of the femur. J. Bone Joint Surg. 42 (1960) 28-30.). The basic structure of PMMA bone cements has basically remained unchanged ever since. PMMA bone cements consist of a liquid monomer component and a powder component. The monomer component generally contains the monomer, methylmethacrylate, and an activator (N,N-dimethyl-p-toluidine) dissolved therein. The powder component consists of one or more polymers that are made by polymerisation, preferably suspension polymerisation, based on methylmethacrylate and co-monomers, such as styrene, methylacrylate or similar monomers, a radio-opaquer, and the initiator, dibenzoylperoxide. When mixing the powder component with the monomer component, swelling of the polymers of the powder component in the methylmethacrylate leads to the formation of a dough that can be shaped plastically. Simultaneously, the activator, N,N-dimethyl-p-toluidine, reacts with the dibenzoylperoxide which decomposes while forming radicals. The radicals thus formed initiate the radical polymerisation of the methylmethacrylate. Upon advancing polymerisation of the methylmethacrylate, the viscosity of the cement dough increases until the cement dough solidifies and is thus cured.

Fundamental mechanical requirements for PMMA bone cements, such as 4-point flexural strength, flexural modulus, and compressive strength, are described in ISO 5833. To the user of PMMA bone cements, the feature of the bone cement to be tack-free has essential importance. The term, tack-free, is defined in ISO5833. In conventional PMMA bone cements, being tack-free indicates that the cement has reached the processing phase through swelling of the polymers contained in the cement powder in the monomer after the components are mixed. A PMMA bone cement must be tack-free as a matter of principle, to allow the user to shape and apply the cement. The PMMA bone cement must not adhere to the gloves and to application aids, such as mixing systems, crucibles or spatulas.

One disadvantage of the conventional PMMA bone cements for cement producers is that both the powder component and the monomer component each need to be manufactured such that they are doubly sterile-packaged. This means that at least four sterile packaging means are required for each package of bone cement.

Another disadvantage of the previous PMMA bone cements for the medical user is that the liquid monomer component needs to be mixed with the powder component in a mixing system or in crucibles right before application of the cement. Mixing errors that easily occur in this process can adversely affect the quality of the cement. After mixing the monomer component with the powder component, there is a need to wait for a certain time depending on the type of cement until the cement dough is tack-free and can be applied. Subsequently, the user has more or less processing time available in which total endoprostheses can be positioned or bone cavities can be filled, like in kyphoplasty and vertebroplasty. During the processing time, the viscosity of the cement dough changes due to the progressive swelling of the polymer particles in the monomer and advancing polymerisation of the monomer. The relatively short processing time is a major disadvantage of the previous bone cements.

Short processing times are particularly disadvantageous in kyphoplasty and vertebroplasty. It would be desirable, in particular for vertebroplasty and kyphoplasty, to have a cement in which the viscosity of the cement dough remains constant over time while the cement is being applied. After application is completed, the cement should be curable instantaneously in a targeted fashion without an additional waiting phase.

It is therefore the object of the invention to develop a PMMA bone cement that alleviates or eliminates the disadvantages of the known PMMA bone cements.

The PMMA bone cement to be developed shall, in particular, be provided to the user in a form such that cumbersome mixing of cement components, which is associated with many possibilities of errors, is avoided. The bone cement shall be as easily as possible to apply. The cement shall be provided such that a waiting phase until it is tack-free is not required. The viscosity and cohesion of the cement dough must be such that it withstands the bleeding pressure until it is cured. Moreover, exposure of the user to monomer vapours shall be avoided as much as possible. Another object is that the PMMA bone cement can be made to cure in a targeted fashion by an external influence.

The object of the invention is met by one-component bone cement pastes according to claim 1. Advantageous further developments are evident from the further claims.

Preferred components of the bone cement pastes are:
AI. at least one methacrylate monomer that is suited for radical polymerisation;
AII. at least one polymer that is soluble in AI;
AIII. at least one particulate polymer that is insoluble in AI and has a particle size of less than 500 μm;
AIV. at least one initiator that can be activated, in particular at least one radical-forming initiator or at least one radical initiator that is soluble in AI and subject to thermal decomposition;
AV. at least one electrically conductive radio-opaquer, in particular in the form of ferromagnetic particles.

Bifunctional methacrylates are preferred as methacrylate monomers, in particular ethylene glycol dimethacrylate, butan-1,3-diol-dimethacrylate, butan-1,4-diol-dimethacrylate, and hexan-1,6-diol-dimethacrylate. These monomers polymerise very quickly after initiation and have boiling points higher than 110° C. under normal pressure, and low volatility. Aside form its high boiling point, hexan-1,6-diol-dimethacrylate has the essential advantage that it is basically insoluble in water at room temperature. It is also feasible to integrate additional monomers with bonding groups into the PMMA bone cement, such as, e.g., methacrylic acid-2-hydroxyethylester. This allows for a targeted influence to be exerted on the bonding of the PMMA bone cement to the articular endoprostheses.

Poly-methylmethacrylate co-polymers are preferred as polymers that are soluble in the methacrylate monomer/methacrylate monomers, in particular poly-methylmethacrylate-co-methylacrylate and poly-methylmethacrylate-co-styrene.

Moreover, cross-linked poly-methylmethacrylate and cross-linked poly-methylmethacrylate-co-methylacrylate are preferred as particulate polymer that is insoluble in the methacrylate monomer/methacrylate monomers.

Initiators that are subject to thermal decomposition are known to the expert. Common examples include peroxides such as dibenzoylperoxide and dilauroylperoxide. Azo compounds are preferred, and of these in particular 2,2'-azobis (isobutyronitrile). In addition, it is also feasible to use other azo initiators possessing a lower or higher decomposition temperature than 2,2'-azobis(isobutyronitrile).

Preferred weight fractions in the paste-like one-component bone cement are 2.0-20.0 parts by weight electrically conductive radio-opaquer; 25.0-45.0 parts by weight methacrylate monomer/methacrylate monomers; 2.0-35.0 parts by weight soluble polymers; 30.0-70.0 parts by weight insoluble polymers, and 0.5-4.0 parts by weight initiator that is subject to thermal decomposition.

Particularly well-suited as electrically conductive radio-opaquers are particles of cobalt, iron, NdFeB, SmCo, cobalt-chromium steel, zirconium, hafnium, titanium, titanium-aluminium-silicon alloys, and titanium-niobium alloys with a particle size of 0.5-500 μm. Eddy currents can be induced in the electrically conductive radio-opaquer by alternating magnetic fields. Additional conventional radio-opaquers can be contained in the paste-like one-component bone cement, in particular zirconium dioxide, barium sulfate, tantalum, and biocompatible calcium salts.

Ferromagnetic particles are particularly preferred as electrically conductive radio-opaquers.

In addition, pharmaceutical excipients can be contained therein, in particular from the group of antibiotics, hormones, growth factors, and antiphlogistics. In consideration as antibiotics are mainly aminoglycoside antibiotics, glycopeptide antibiotics, fluoroquinolone antibiotics, lincosamide antibiotics, and oxazolidinone antibiotics. Preferred in this context are gentamicin, tobramycin, amikacin, teicoplanin, vancomycin, ramoplanin, dalbavancin, moxifloxacin, ciprofloxacin, lincosamin, clindamycin, and linezolide. The antibiotics can be present in the paste-like one-component bone cement in particulate or in dissolved form.

In addition, one or more biocompatible elastomers that are particulate or soluble in the methacrylate monomer/methacrylate monomers can be contained therein, in particular polybutadiene-co-styrene. This allows for the production of particularly impact-resistant and fatigue-resistant cements.

Moreover, if applicable, an electrically conductive additive can be contained therein in order to improve the contacting of the radio-opaquer particles. Additives of this type that are in consideration are nanoparticulate metal particles, conductive polymers, and graphite.

Bone cement pastes according to the invention can be used as self-curing plastic materials for the fixation of primary total articular endoprostheses and of revision articular endoprostheses, moreover as self-curing filling materials for vertebroplasty, kyphoplasty, and for femoral neck augmentation or also as self-curing implant materials for the production of local agent release systems. Accordingly, it is feasible, e.g., to use an antibiotic-containing PMMA bone cement according to the invention to form sphere-shaped or bean-shaped implants that can be used as local agent release systems.

The PMMA bone cement paste can also be used for producing further one-component bone cements. For this purpose, it is advantageous to dissolve or suspend in the PMMA bone cement paste a radical initiator that can be activated externally, e.g. a photoinitiator or a photoinitiator system. It is also feasible to provide an initiator or initiators where there is transient contact with the paste, such as in a part of the container, a dosing facility or a transport cannula.

In particular, the PMMA bone cement paste is free of acids or acid group-containing monomers.

The invention is also related to a method for curing the paste-like one-component bone cement, in which the paste-like bone cement is exposed to an alternating magnetic field with a frequency in the range of 500 Hz to 50 kHz. This induces eddy currents in the radio-opaquer that cause the opaquer to heat up. Through heat transfer, the initiator is also heated up and made to thermally decompose. Radical polymerisation of the methacrylate monomer/methacrylate monomers then commences and leads to curing of the cement. The particular advantage of inductive heating is that only electrically conductive materials can heat up due to the induction of eddy currents, whereas human tissue is not heated up by alternating magnetic fields.

In a further method for curing the paste-like one-component bone cement, the paste-like bone cement can be heated by induction until the decomposition of the initiator commences.

This generally results in a
method for curing pastes containing
at least one initiator that can be activated, in particular at least one radical-forming initiator or at least one radical initiator that is subject to thermal decomposition; and
at least electrically conductive particles, in particular ferromagnetic particles,
whereby the paste is exposed to an alternating magnetic field with a frequency in the range of 500 Hz to 50 kHz, or
whereby the paste is heated by induction until thermal decomposition of the initiator commences. This can be applied, in particular, in dental pastes.

The invention is illustrated by the examples presented in the following without limiting the scope of the invention. Like in the other parts of the description, specification of parts and percentages refers to the weight unless specified otherwise.

EXAMPLE 1

Pastes 1-5

A particulate poly-methylmethacrylate-co-methylacrylate (molecular mass approx. 800,000; approx. 5-8% methylacrylate fraction, grain size <63 μm), hereinafter called polymer 1, was used for the pastes described in the following. This polymer is insoluble in hexan-1,6-diol-dimethacrylate and in butan-1,4-diol-dimethacrylate. Moreover, a poly-methylmethacrylate-co-methylacrylate (molecular mass approx. 600,000; approx. 50% methylacrylate fraction) was used. This polymer is soluble in hexan-1,6-diol-dimethacrylate and in butan-1,4-diol-dimethacrylate.

In each case, polymer 2 was first dissolved in the appropriate quantity of hexan-1,6-diol-dimethacrylate. Polymer 1 was then added to these solutions by kneading at room temperature. The pastes were tack-free and brush-applicable. They showed no further volume change from 48 hours after their production.

| Paste components | Composition | | | | |
| --- | --- | --- | --- | --- | --- |
| | Paste 1 | Paste 2 | Paste 3 | Paste 4 | Paste 5 |
| Polymer 1 | 20.000 g | 20.000 g | 20.000 g | 15.950 g | 21.312 g |
| Polymer 2 | 1.785 g | 1.190 g | 0.833 g | 2.392 g | 1.588 g |
| Hexan-1,6-diol-dimethacrylate | 10.115 | 10.710 g | 11.067 g | 13.557 g | 9.000 g |

EXAMPLE 2

Pastes 6-10

The preparation process was analogous to pastes 1-5 except for the use of butan-1,4-diol-dimethacrylate.

| Paste components | Composition | | | | |
|---|---|---|---|---|---|
| | Paste 6 | Paste 7 | Paste 8 | Paste 9 | Paste 10 |
| Polymer 1 | 20.000 g | 20.000 g | 20.000 g | 15.950 g | 21.312 g |
| Polymer 2 | 1.785 g | 1.190 g | 0.833 g | 2.392 g | 1.588 g |
| Hexan-1,6-diol-dimethacrylate | 10.115 | 10.710 g | 11.067 g | 13.557 g | 9.000 g |

The pastes were tack-free and brush-applicable. They showed no further volume change from 48 hours after their production.

EXAMPLE 3

Two-Component Paste Cement

The preparation process was analogous to that of pastes 1-10 based on the recipe of paste 1. However, the initiation system used in this case was CaCHEBA (calcium salt of 1-cyclohexyl-5-ethyl-barbituric acid)/copper carbonate/ALIQUAT/2-ethyl-hexanoic acid. Pastes A and B were tack-free, brush-applicable, and homogeneous to the eye.

| Paste components | Composition | |
|---|---|---|
| | Paste A | Paste B |
| Polymer 1 | 4.998 g | 5.250 g |
| Polymer solution | 3.500 g | 3.500 g |
| Mixture of zirconium dioxide and copper carbonate | 1.002 g | — |
| Zirconium dioxide | — | 1.000 g |
| CaCHEBA | 0.500 g | |
| 2-Ethyl-hexanoic acid | — | 0.200 g |
| ALIQUAT 336 | — | 0.050 g |

After mixing of components A and B, the resulting paste was also easy to shape and brush-applicable without difficulty. The curing started 2 minutes and 50 seconds after the mixing.

EXAMPLE 4

Two-Component Paste Cement

| Paste components | Composition | |
|---|---|---|
| | Paste A | Paste B |
| Degacryl 6690 | 4.998 g | 5.250 g |
| Polymer solution | 3.500 g | 3.500 g |
| Mixture of zirconium dioxide and copper carbonate | 0.501 g | — |
| Zirconium dioxide | 0.501 g | 1.000 g |
| CaCHEBA | 0.500 g | |
| 2-Ethyl-hexanoic acid | — | 0.200 g |
| ALIQUAT 336 | — | 0.050 g |

Degacryl 6690 is a cross-linked polymethylmethacrylate. A tack-free paste resulted after the mixing of the tack-free components, A and B. The curing started 4 minutes and 5 seconds after the mixing of components A and B.

The invention claimed is:

1. A one-component polymethylmethacrylate bone cement paste consisting of (i) at least one methacrylate monomer selected from the group consisting of butan-1,3-diol-dimethacrylate, butan-1,4-diol-dimethacrylate, and hexan-1,6-diol-dimethacrylate;
(ii) at least one polymer that is soluble in the methacrylate monomer;
(iii) at least one particulate polymer selected from the group consisting of cross-linked poly-methylmethacrylate and cross-linked poly-methylmethacrylate-co-methylacrylate, wherein the particulate polymer is insoluble in the methacrylate monomer and having a particle size of less than 500 µm;
(iv) at least one radical initiator that is soluble in the methacrylate monomer and subject to thermal decomposition;
(v) at least one electrically conductive radio-opaquer;
(vi) optionally at least one additional radio-opaquer;
(vii) optionally at least one pharmaceutical agent; and
(viii) optionally at least one biocompatible elastomer that is particulate or soluble in the methacrylate monomer/methacrylate monomers;

wherein the ratio of said at least one methacrylate monomer to soluble polymer to particulate insoluble polymer to radical initiator to electrically conductive radio-opaquer is 25-50:2-35:40-70:0.5-4.0:2.0-20 based on the weight of the paste.

2. Bone cement paste according to claim 1, wherein said at least one radical initiator that is soluble in the methacrylate monomer and subject to thermal decomposition can be activated.

3. Bone cement paste according to claim 1, wherein said electrically conductive radio-opaquer is present and are particles having a particle size of 0.5 to 500 µm of cobalt, iron, NdFeB, SmCo, cobalt-chromium steel, zirconium, hafnium, titanium, titanium-aluminum-silicon alloys, or titanium-niobium alloys.

4. Bone cement paste according to claim 3, wherein said electrical conductive radio-opaquer is iron in the form of ferromagnetic particles.

5. Bone cement paste according to claim 1, wherein the methacrylate monomer is suited for distillation.

6. Bone cement paste according to claim 1, wherein the soluble polymer is a poly-methylmethacrylate-co-polymer.

7. Bone cement paste according to claim 6, wherein the soluble polymer is poly-methylmethacrylate-co-methylacrylate or poly-methyl methacrylate-co-styrene.

8. Bone cement paste according to claim 1, wherein said at least one additional radio-opaquer is present and is selected from the group consisting of zirconium dioxide, barium sulfate, tantalum, and biocompatible calcium salts.

9. Bone cement paste according to claim 1, wherein said at least one pharmaceutical agent is present and is selected from the group consisting of antibiotics, hormones, growth factors, and antiphlogistics.

10. Bone cement paste according to claim 1, wherein said at least one biocompatible elastomer that is particulate or soluble in the methacrylate monomer is present.

11. Bone cement paste according to claim 10, wherein said biocompatible elastomer is polybutadiene or poly-butadiene-co-styrene.

12. Method for curing a bone cement paste comprising exposing a bone cement paste according to claim 1 to an alternating magnetic field with a frequency in the range of 500 Hz to 50 kHz.

13. Method for curing a bone cement paste comprising heating a bone cement paste according to claim 2 by induction until the decomposition of the initiator commences.

\* \* \* \* \*